June 10, 1958 E. C. BOSLEY Plant Pat. 1,717
AZALEA PLANT
Filed Oct. 15, 1957
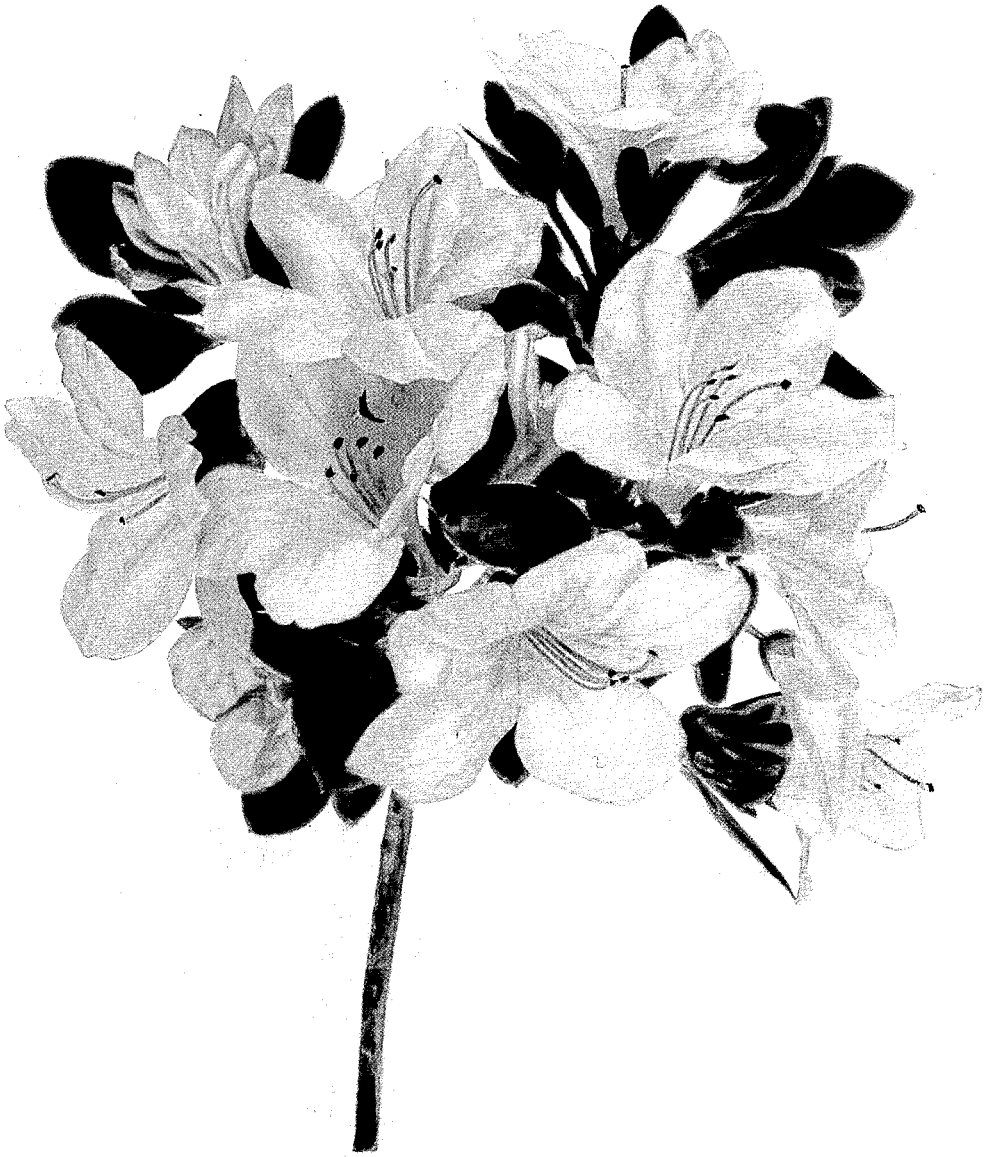
INVENTOR
Edith C. Bosley
By Orville M. Kile
Plant Patent Agent.

United States Patent Office

Plant Pat. 1,717
Patented June 10, 1958

1,717

AZALEA PLANT

Edith C. Bosley, Mentor, Ohio

Application October 15, 1957, Serial No. 690,414

1 Claim. (Cl. 47—60)

My present invention relates to a new and distinct variety of azalea plant of the semi-evergreen Kaempferi type, but with lower growth than is usual with that class. It originated as a seedling in our nursery, located in Mentor, Ohio, of which I am operating partner, and is the result of breeding efforts on my part. However, the records have been destroyed on this and other seedlings produced at that time and I therefore do not know the parentage of my new variety.

The most outstanding features of my new variety are its compact growth, its extreme hardiness, and its intensely red blooms that resist fading.

I have asexually reproduced this new variety at our nursery, by means of cuttings, and its distinguishing features appear to be permanent.

The accompanying illustration shows a branch or truss of the blooms and leaves, in approximately their true colors.

In the following detailed description, color plate numbers indicate Ridgway's Color Standards and Nomenclature, while other color names used indicate the usual dictionary meaning of the term.

*The plant*

Growth: Under average conditions a ten-year-old plant would be approximately 2½ feet broad by 15 inches high. The bush grows dense and compact and its breadth is about 2 to 2½ times the height. Rate of growth is approximately one-half that of the standard Kaempferi hybrids.

Hardiness: The plant is exceptionally wood hardy, having withstood temperatures as low as 15 degrees below zero F. Buds are not hardy at such low temperatures but are hardy at an occasional 5 degrees below zero F.

Blooming habit: Very prolific producer of good blooms.

Blooming season: Average season begins the second week in May.

Stems: Woody; sturdy; approximately Medal Bronze (Pl. IV).

Foliage:

*Size.*—Largest leaves are about 1½ inches long and ¾ inch wide.

*Type.*—Semi-evergreen, making an excellent decorative plant even when not in bloom.

*Color.*—Young leaves are light green, approximately Courge Green (Pl. XVII); mature leaves, Dusky Olive Green (Pl. XLI) in tone but bright and glossy.

*Shape.*—Oval.

*Texture.*—Heavy.

*Margin.*—Smooth.

*Appearance.*—Glossy on upper surface; dull on under surface.

*The bloom*

Bud:

*Shape.*—Long and pointed.

*Color.*—Approximately Scarlet Red (Pl. I).

Flower:

*Borne.*—In truss formation.

*Form.*—Single; five petals forming a deep funnel.

*Texture.*—Substantial.

*Size.*—Diameter is 1½ to 2 inches.

*Color.*—Almost a pure Scarlet Red (Pl. I). Unlike other red-flowered azaleas, many of which fade after 6 to 8 hours in bright sunlight, the color of my variety does not fade for many days. The flower usually lasts for about two weeks and remains bright the entire time.

*Aspect.*—Silky.

*Persistence.*—Flowers last about two weeks dropping off cleanly, leaving pistil and stamens attached.

Reproductive organs: Both pistils and stamens extend beyond the tube portion of the flower—all gracefully curved. Styles and filaments are approximately Carmine (Pl. I) with stigmas and anthers Dark Perilla Purple (Pl. XXXVII). The deep coloring of these parts adds greatly to the pleasing appearance of the flower.

Having thus disclosed my invention, I claim:

The new and distinct variety of azalea plant, substantially as herein shown and described, characterized particularly by its low, compact growth; its semi-evergreen foliage; its exceptional hardiness; and its crimson red flowers which do not fade.

No references cited.